US 12,232,859 B2

(12) United States Patent
Kato

(10) Patent No.: US 12,232,859 B2
(45) Date of Patent: Feb. 25, 2025

(54) MAGNETIC RESONANCE IMAGING APPARATUS

(71) Applicant: CANON MEDICAL SYSTEMS CORPORATION, Otawara (JP)

(72) Inventor: Sojuro Kato, Kawasaki (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 167 days.

(21) Appl. No.: 18/189,517

(22) Filed: Mar. 24, 2023

(65) Prior Publication Data

US 2023/0320614 A1 Oct. 12, 2023

(30) Foreign Application Priority Data

Mar. 29, 2022 (JP) ................................. 2022-053700

(51) Int. Cl.
*G01R 33/36* (2006.01)
*A61B 5/00* (2006.01)
*A61B 5/055* (2006.01)

(52) U.S. Cl.
CPC ................ *A61B 5/055* (2013.01); *A61B 5/72* (2013.01); *G01R 33/3692* (2013.01)

(58) Field of Classification Search
CPC ........ A61B 5/055; A61B 5/72; G01R 33/3692
See application file for complete search history.

(56) References Cited

U.S. PATENT DOCUMENTS

2016/0169991 A1* 6/2016 Kato .................. G01R 33/3692
324/322

FOREIGN PATENT DOCUMENTS

JP 2016-112037 A 6/2016

* cited by examiner

*Primary Examiner* — G. M. A Hyder
(74) *Attorney, Agent, or Firm* — Oblon, McClelland, Maier & Neustadt, L.L.P.

(57) ABSTRACT

A magnetic resonance imaging apparatus of an embodiment includes a transmission coil, a reception coil, and first processing circuitry. The transmission coil radiates RF pulses to a subject. The reception coil receives magnetic resonance signals from the subject. The first processing circuitry controls the transmission coil and the reception coil. The reception coil includes a clock receptor, a phase synchronizer, and second processing circuitry. The clock receptor receives a clock signal wirelessly transmitted by the first processing circuitry. The phase synchronizer performs phase synchronization with the clock signal. The second processing circuitry controls the phase synchronizer. The second processing circuitry switches operating states of the phase synchronizer in accordance with a radiation timing of the RF pulses.

7 Claims, 6 Drawing Sheets

MAGNETIC RESONANCE IMAGING APPARATUS

CROSS-REFERENCE TO RELATED APPLICATION

The present application claims priority based on Japanese Patent Application No. 2022-053700, filed Mar. 29, 2022, the content of which is incorporated herein by reference.

FIELD

Embodiments of the present invention relate to a magnetic resonance imaging apparatus.

BACKGROUND

A magnetic resonance imaging (MRI) apparatus has been used as a medical diagnostic apparatus that performs diagnosis using images. A magnetic resonance imaging apparatus (hereinafter referred to as an "MRI apparatus") captures tomographic images of a subject by receiving MR signals excited by radio frequency (RF) pulses radiated in a strong magnetic field through an RF coil. In recent years, making a wireless type RF coil attached to a subject wireless in MRI apparatuses has been conceived.

When a wireless type RF coil is adopted, in order to synchronize a clock signal in the wireless type RF coil with a system clock signal of the main body of an MRI apparatus, the clock signal needs to be wirelessly transmitted from the main body side of the MRI apparatus to the wireless type RF coil side. However, the MRI apparatus, in principle, radiates strong RF pulses. For this reason, the radiated RF pulses affect the clock signal transmitted wirelessly, which may cause the clock signals to be out of synchronization in the wireless type RF coil or increase fluctuation (jitter) in the clock signals.

DETAILED DESCRIPTION

A magnetic resonance imaging apparatus of an embodiment includes a transmission coil, a reception coil, and first processing circuitry. The transmission coil radiates RF pulses to a subject. The reception coil receives magnetic resonance signals from the subject. The first processing circuitry controls the transmission coil and the reception coil. The reception coil includes a clock receptor, a phase synchronizer, and second processing circuitry. The clock receptor receives a clock signal wirelessly transmitted by the first processing circuitry. The phase synchronizer performs phase synchronization with the clock signal. The second processing circuitry controls the phase synchronizer. The second processing circuitry switches operating states of the phase synchronizer in accordance with a radiation timing of the RF pulses.

A magnetic resonance imaging apparatus according to an embodiment will be described below with reference to the drawings.

A magnetic resonance imaging (MRI) apparatus (hereinafter referred to as an "MRI apparatus") is a medical diagnostic apparatus that captures tomographic image (hereinafter referred to as an "MR image") of a subject (e.g., a human body) by radiating radio frequency (RF) pulses in a state in which a strong magnetic field is applied to the subject, receiving electromagnetic waves generated from hydrogen nuclei in the body of the subject due to the nuclear magnetic resonance phenomenon through an RF coil, and reconstructing nuclear magnetic resonance signals (hereinafter referred to as "MR signals") based on the received electromagnetic waves. An MRI apparatus can also capture an MR image of a subject by reconstructing MR signals based on electromagnetic waves received through a wireless type RF coil attached to the subject. An MRI apparatus displays an MR image of a subject such that a person who performs MRI examination (a doctor, an engineer, or the like) can visually check whether or not the subject has a lesion.

Figure 1:
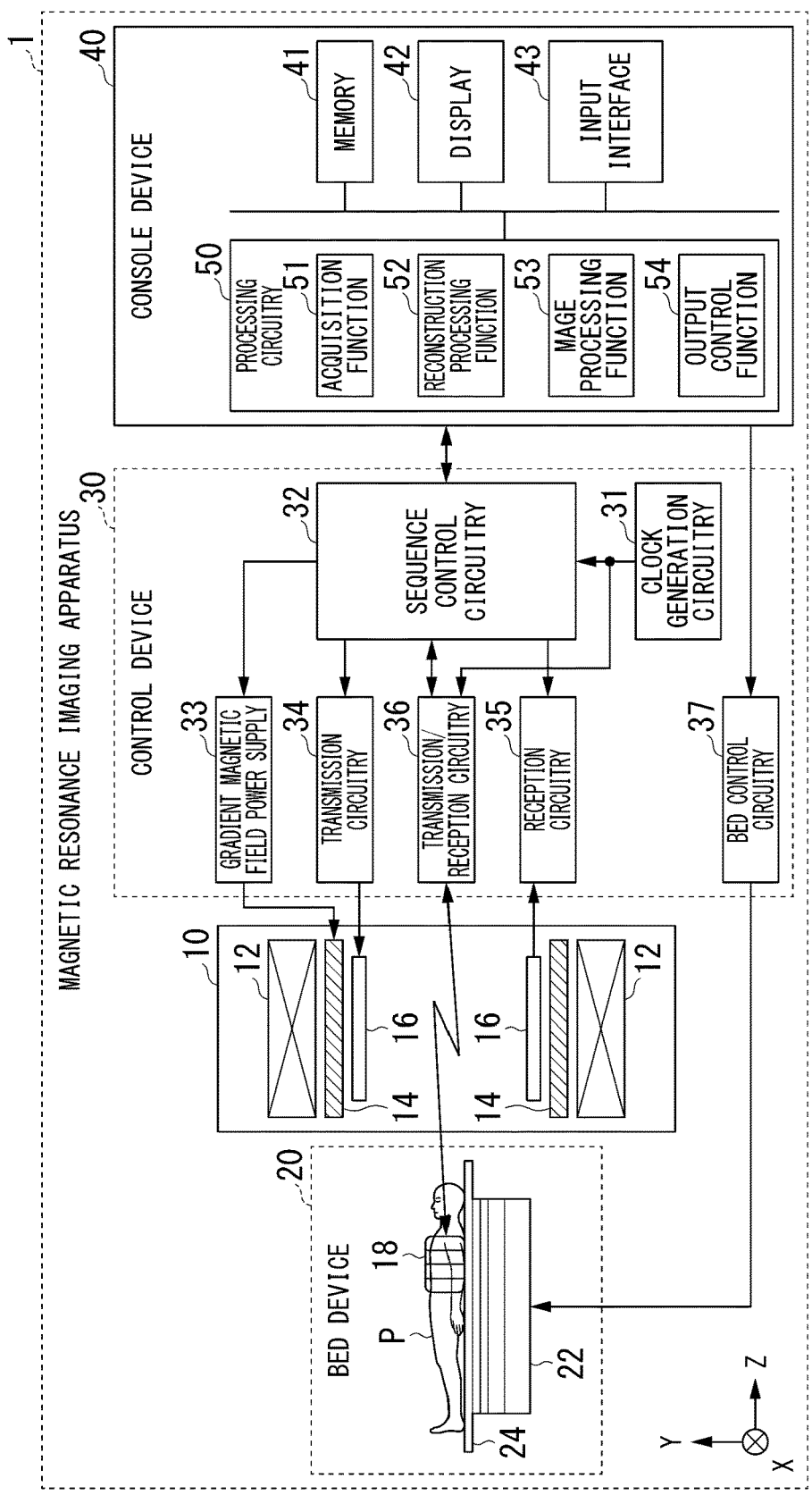
FIG. 1 is a diagram showing an example of a configuration of a magnetic resonance imaging apparatus according to an embodiment.

FIG. 1 is a diagram showing an example of a configuration of a magnetic resonance imaging apparatus (MRI apparatus) according to an embodiment. The MRI apparatus 1 includes, for example, a gantry device 10, a bed device 20, a control device 30, and a console device 40. Although the control device 30 and the console device 40 are separate from the gantry device 10 in the description of the present embodiment, the gantry device 10 may include some or all of the components of the control device 30 and the console device 40. The MRI apparatus 1 is an example of a "magnetic resonance imaging apparatus."

The gantry device 10 includes, for example, a static magnetic field magnet 12, a gradient magnetic field coil 14, and an RF coil 16. Further, the gantry device 10 includes, as a component of the RF coil 16, a wireless type RF coil 18 (hereinafter referred to as a "wireless RF coil 18") that can be attached to a subject P, for example. The static magnetic field magnet 12 is a magnet formed in a substantially cylindrical hollow shape. The static magnetic field magnet 12 generates a uniform static magnetic field in the internal space. The static magnetic field magnet 12 is, for example, a permanent magnet, a superconducting magnet, or the like. When the static magnetic field magnet 12 is a superconducting magnet, it receives power from a static magnetic field power supply (not shown) to generate a static magnetic field.

The gradient magnetic field coil 14 is a coil formed in a substantially cylindrical hollow shape. The gradient magnetic field coil 14 is disposed inside the static magnetic field magnet 12. The gradient magnetic field coil 14 is formed by combining three coils corresponding to mutually orthogonal X, Y, and Z axes. The three coils corresponding to the direction of each axis are individually supplied with a current from a gradient magnetic field power supply 33 and generate a gradient magnetic field in which the magnetic field strength varies along each of the X axis, Y axis and Z axis in an imaging space of the MRI apparatus 1 in which the subject P has been introduced. In the present embodiment, the central axis of the gantry device 10 or the longitudinal direction of a top board 24 of the bed device 20 is defined as a Z-axis direction, an axis orthogonal to the Z-axis direction and horizontal to the floor surface of the room in which the MRI apparatus 1 is installed is defined as an X-axis direction, and a direction orthogonal to the Z-axis direction and perpendicular to the floor surface is defined as a Y-axis direction. In the present embodiment, the Z-axis direction is the same direction as the static magnetic field.

Here, gradient magnetic fields along the X axis, Y axis, and Z axis generated by the gradient magnetic field coil 14 correspond to a slice selection gradient magnetic field, a phase encoding gradient magnetic field, and a readout gradient magnetic field, for example. The slice selection gradient magnetic field is used to determine an arbitrary imaging section in the MRI apparatus 1. The phase encoding gradient magnetic field is used to change the phase of an MR signal according to a spatial position in the MRI apparatus 1. The readout gradient magnetic field is used to change the frequency of an MR signal according to a spatial position in the MRI apparatus 1.

The RF coil 16 is a whole-body coil that is housed in the gantry device 10 and configured to surround the subject P within the imaging space. The RF coil 16 is supplied with RF pulses from a transmission circuitry 34 and generates a high frequency magnetic field. The RF coil 16 receives MR signals emitted from the subject P according to the influence of the high frequency magnetic field. Upon receiving the MR signals, the RF coil 16 outputs the received MR signals to a reception circuitry 35. The RF coil 16 may perform transmission of RF pulses and reception of MR signals using different RF coil configurations or may perform the same using the same RF coil configuration, that is, a configuration for both transmission and reception. The RF coil 16 may be, for example, a coil array composed of a plurality of coil elements. The RF coil 16 is an example of a "transmission coil."

The wireless RF coil 18 is a wireless type local coil attached to the subject P. The wireless RF coil 18 has various shapes depending on a part of the subject P to be imaged. FIG. 1 shows an example of the wireless RF coil 18 attached to the body of the subject P. The wireless RF coil 18 receives MR signals emitted from the subject P according to the influence of the high frequency magnetic field generated by the RF coil 16 and transmits data representing the received MR signals (hereinafter referred to as "MR data") to a transmission/reception circuitry 36. The wireless RF coil 18 may also be, for example, a coil array composed of a plurality of coil elements. The wireless RF coil 18 is an example of a "reception coil."

The bed device 20 moves the subject P, which is an imaging target, placed thereon and introduces the subject P into the inside of the gantry device 10 (into the cavity of the static magnetic field magnet 12, the gradient magnetic field coil 14, and the RF coil 16, that is, an imaging port). The bed device 20 includes, for example, a base 22 and the top board 24.

The base 22 moves the top board 24 on which the subject P is placed in the vertical direction of the top board 24 (Y-axis direction) or the longitudinal direction of the top board 24 (Z-axis direction) according to operation of a bed driving device (not shown) that operates in response to a control signal output from a bed control circuitry 37. The base 22 includes a housing that movably supports the top board 24. The bed driving device (not shown) includes, for example, a motor and an actuator. The bed driving device (not shown) may move not only the top board 24 but also the base 22 itself in the longitudinal direction of the top board 24. When the gantry device 10 is configured to be movable in the Z-axis direction, the bed driving device (not shown) may operate to move the gantry device 10 such that the subject P is introduced into the gantry device 10. When both the gantry device 10 and the top board 24 and the base 22 are movable, the bed driving device (not shown) may operate to move the gantry device 10, 5 the top board 24 and the base 22 such that the subject P is introduced into the gantry device 10. The top board 24 is a plate-like member on which the subject P is placed.

The control device 30 controls the operations of the gantry device 10 and the bed device 20 according to control of the console device 40. The control device 30 includes, for example, a clock generation circuitry 31, a sequence control circuitry 32, the gradient magnetic field power supply 33, the transmission circuitry 34, the reception circuitry 35, the transmission/reception circuitry 36, and the bed control circuitry 37. The control device 30 may be provided inside the gantry device 10 or may be provided inside the console device 40. The control device 30 is an example of a "first processing circuitry."

The clock generation circuitry 31 generates a clock signal serving as a reference for an operation of imaging the subject P in the MRI apparatus 1. The clock generation circuitry 31 includes, for example, a clock oscillator. The clock generation circuitry 31 outputs the generated clock signal to each component.

The sequence control circuitry 32 is a sequencer that performs imaging of the subject P by driving the gradient magnetic field power supply 33, the transmission circuitry 34, and the reception circuitry 35 on the basis of sequence information set by the console device 40. The sequence control circuitry 32 may be, for example, processing circuitry having a processor such as a central processing unit (CPU). The sequence information is information in which a procedure for performing imaging processing for imaging the subject P in the MRI apparatus 1 is defined in advance. In the sequence information, for example, the operations of the gradient magnetic field power supply 33, the transmission circuitry 34, and the reception circuitry 35 at the time of imaging the subject P and operation timings thereof (hereinafter referred to as "events") are represented in chronological order. More specifically, the magnitude of a current supplied to the gradient magnetic field coil 14 by the gradient magnetic field power supply 33 and a current supply timing, the intensity of RF pulses transmitted (supplied) to the RF coil 16 by the transmission circuitry 34 and an RF pulse supply timing, a timing of receiving (detecting) an MR signal output by the RF coil 16 to the reception circuitry 35, and the like are represented as events in the sequence information. The sequence control circuitry 32 sequentially executes the events represented by the sequence information to drive the gradient magnetic field power supply 33, the transmission circuitry 34, and the reception circuitry 35, and when the reception circuitry 35 receives an MR signal, transfers the received MR signal (more specifically, MR data output by the reception circuitry 35) to the console device 40.

Furthermore, the sequence control circuitry 32 causes the transmission/reception circuitry 36 to transmit the clock signal generated by the clock generation circuitry 31 and sequence data for driving the wireless RF coil 18. The clock signal is a clock signal used (as a reference) when the sequence control circuitry 32 drives the gradient magnetic field power supply 33, the transmission circuitry 34, and the reception circuitry 35, and the wireless RF coil 18 also operates in synchronization with the gradient magnetic field power supply 33, the transmission circuitry 34, and the reception circuitry 35 by operating on the basis of the transmitted clock signal. In other words, the sequence data is a timetable showing time information for causing the wireless RF coil 18 to image the subject P. The sequence data represents time information for the wireless RF coil 18 to perform imaging of the subject P in synchronization with events represented by the sequence information in chronological order on the basis of a time at which imaging of the subject P is started in the MRI apparatus 1, that is, a time at which the sequence control circuitry 32 starts to drive the gradient magnetic field power supply 33, the transmission circuitry 34, and the reception circuitry 35. More specifically, the sequence data represents a time at which the RF coil 16 starts to radiate RF pulses, an RF pulse radiation period, the intensity of the radiated RF pulses, a time at which the wireless RF coil 18 starts to detect an MR signal, a duration thereof, and the like using the time at which imaging of the subject Pis started as a reference time (time=0). The sequence control circuitry 32 causes the transmission/reception circuitry 36 to transmit a clock signal to transmit event data to the wireless RF coil 18 before driving the gradient magnetic field power supply 33, the transmission circuitry 34, and the reception circuitry 35 on the basis of the sequence information, that is, starting imaging of the subject Pin the MRI apparatus 1. When the transmission/reception circuitry 36 receives MR data, the sequence control circuitry 32 transfers the received MR data to the console device 40.

The gradient magnetic field power supply 33 supplies a current individually to each of the three coils in the gradient magnetic field coil 14 which correspond to the directions of the respective axes.

The transmission circuitry 34 supplies RF pulses to the RF coil 16. The RF pulses supplied to the RF coil 16 by the transmission circuitry 34 are pulses corresponding to a Larmor frequency determined by the type of an atomic nucleus that is a target and the strength of magnetic fields.

The reception circuitry 35 detects the MR signal output by the RF coil 16 and generates MR data representing the detected MR signal. The reception circuitry 35 generates MR data by converting the MR signal into digital data, for example. The reception circuitry 35 outputs the generated MR data to the sequence control circuitry 32. The sequence control circuitry 32 transfers the MR data output by the reception circuitry 35 to the console device 40.

The transmission/reception circuitry 36 transmits the clock signal generated by the clock generation circuitry 31 and the sequence data output by the sequence control circuitry 32 to the wireless RF coil 18 according to the control of the sequence control circuitry 32. The transmission/reception circuitry 36 receives the MR data transmitted by the wireless RF coil 18. The transmission/reception circuitry 36 outputs the received MR data to the sequence control circuitry 32. The transmission/reception circuitry 36 performs transmission of the clock signal and the sequence data and reception of the MR data, for example, using a wireless communication standard such as Wi-Fi. The transmission/reception circuitry 36 includes, for example, an antenna (not shown) compatible with the wireless communication standard.

The bed control circuitry 37 outputs a control signal for moving the base 22 and the top board 24 on which the subject P is placed to the bed driving device (not shown) included in the bed device 20 according to control of the console device 40. The bed control circuitry 37 may be provided in the gantry device 10 or may be provided in the bed device 20. In this case, the bed control circuitry 37 outputs, to the bed driving device (not shown) included in the bed device 20, a control signal in response to an input signal, which is input from an input interface (not shown) included in the device in which the bed control circuitry 37 is provided when an operator (doctor, engineer, or the like) of the MRI apparatus 1 operates the input interface.

The console device 40 controls the entire MRI apparatus 1 and collects MR data. The console device 40 includes, for example, a memory 41, a display 42, an input interface 43, and processing circuitry 50.

The memory 41 is realized by, for example, a semiconductor memory element such as a read only memory (ROM), a random access memory (RAM), or a flash memory, a hard disk drive (HDD), an optical disc, or the like. The memory 41 stores data such as MR data output by the sequence control circuitry 32 and reconstructed images (MRI images) generated on the basis of the MR data. Such data may be stored in an external memory with which the MRI apparatus 1 can communicate instead of (or in addition to) the memory 41. The external memory is controlled by, for example, receiving a read/write request by a cloud server that manages a network attached storage (NAS) and external memories. The external memory is realized by, for example, a system called picture archiving and communication system (PACSs). The PACS are medical image management systems that systematically store, for example, images captured by various image diagnostic apparatuses.

The display 42 displays various types of information. For example, the display 42 displays images generated by the processing circuitry 50, graphical user interface (GUI) images for receiving various operations by the operator of the MRI apparatus 1, and the like. The display 42 is, for example, a liquid crystal display (LCD), a cathode ray tube (CRT) display, an organic electroluminescence (EL) display, or the like. The display 42 may be provided in the gantry device 10. The display 42 may be of a desktop type or may be a display device (for example, a tablet terminal) capable of wireless communication with the main body of the console device 40.

The input interface 43 receives various input operations by the operator of the MRI apparatus 1 and outputs electrical signals indicating the content of the received input operations to the processing circuitry 50. For example, the input interface 43 receives input operations such as acquisition conditions at the time of acquiring MR data, generation conditions at the time of generating MR data, reconstruction conditions at the time of reconstructing reconstructed images, image processing conditions at the time of generating post-processed images from reconstructed images, and the like. The input interface 43 is realized by, for example, a mouse, a keyboard, a touch panel, a trackball, a switch, a button, a joystick, a camera, an infrared sensor, a microphone, and the like. When the input interface 43 is a touch panel, the display 42 may be formed integrally with the input interface 43. The input interface 43 may be provided in the gantry device 10. The input interface 43 may be realized by a display device (for example, a tablet terminal) capable of wireless communication with the main body of the console device 40. In this specification, the input interface 43 is not limited to one having physical operation components such as the aforementioned mouse and keyboard. For example, examples of the input interface 43 include electrical signal processing circuitry that receives an electrical signal corresponding to an input operation from external input equipment provided separately from the console device 40 and outputs this electrical signal to the processing circuitry 50.

The processing circuitry 50 controls the overall operation of the MRI apparatus 1. The processing circuitry 50 sets sequence information in the sequence control circuitry 32. The processing circuitry 50 executes, for example, an acquisition function 51, a reconstruction processing function 52, an image processing function 53, an output control function 54, and the like. The processing circuitry 50 realizes these functions by, for example, a hardware processor included in a computer device executing a program (software) stored in the memory 41, which is a storage device (storage circuitry).

The hardware processor is, for example, circuitry such as a CPU, a graphics processing unit (GPU), an application specific integrated circuit (ASIC), or a programmable logic device (e.g., a simple programmable logic device (SPLD), a complex programmable logic device (CPLD), or a field programmable gate array (FPGA)). Instead of storing the program in the memory 41, the program may be directly embedded in the circuitry of the hardware processor. In this case, the hardware processor realizes the functions by reading and executing the program embedded in the circuitry. The hardware processor is not limited to being configured as a single circuit, and may be configured as one hardware processor by combining a plurality of independent circuits to realize each function. A plurality of components may be integrated into one hardware processor to realize each function. Each function may be realized by incorporating a plurality of components into one dedicated LSI. Here, the program (software) may be stored in advance in a storage device (a storage device including a non-transitory storage medium) that constitutes the memory 41 such as a ROM, a RAM, an HDD, or a flash memory, or may be stored in a detachable storage medium (non-transitory storage medium) such as a DVD or a CD-ROM and installed in the storage device included in the console device 40 when the storage medium is set in a drive device included in the console device 40. The program (software) may be downloaded in advance from another computer device via a network and installed in the storage device included in console device 40.

Each component included in the console device 40 or the processing circuitry 50 may be distributed and realized by a plurality of pieces of hardware. The processing circuitry 50 may be realized by a processing device capable of communicating with the console device 40 instead of being a component included in the console device 40. The processing device is, for example, a workstation connected to one MRI apparatus, or a device (for example, a cloud server) that is connected to a plurality of MRI apparatuses and collectively executes processing equivalent to the processing circuitry 50 which will be described below. That is, the configuration of the present embodiment can also be realized as an MRI examination system (medical diagnostic system) in which the MRI apparatus and other processing devices are connected via a network.

The acquisition function 51 acquires the MR data transferred by the sequence control circuitry 32. The MR data is an MR signal converted into digital data by the reception circuitry 35 or data received from the wireless RF coil 18 by the transmission/reception circuitry 36.

The reconstruction processing function 52 performs predetermined reconstruction processing on the MR data acquired by the acquisition function 51 to generate a reconstructed image. For example, the reconstruction processing function 52 arranges the MR data in two dimensions or three dimensions corresponding to a slice selection gradient magnetic field, a phase encoding gradient magnetic field, and a readout gradient magnetic field, and then performs reconstruction processing using Fourier transform or the like to generate a reconstructed image. The reconstruction processing function 52 stores the generated reconstructed image in the memory 41.

The image processing function 53 converts the reconstructed image stored in the memory 41 into a three-dimensional image or cross-sectional image data of an arbitrary cross-section by a known method on the basis of an input operation received through the input interface 43. The image processing function 53 stores the converted cross-sectional image data in the memory 41 as an MR image.

Figure 2:
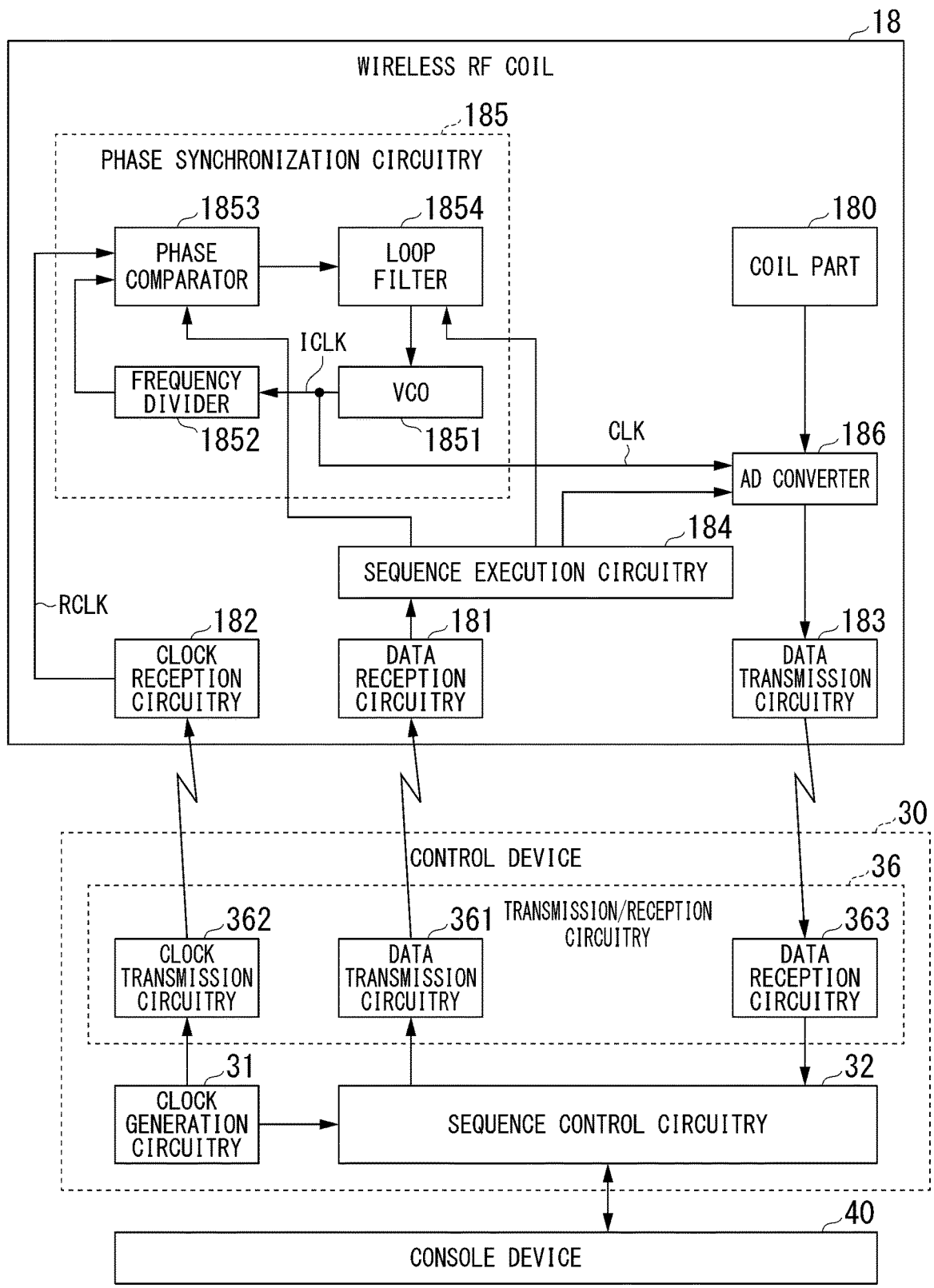
FIG. 2 is a diagram showing an example of a configuration and an example of connection of a wireless RF coil according to an embodiment.

The output control function 54 controls a display mode in the display 42, for example. The output control function 54 outputs the MR image generated by the image processing function 53 and stored in the memory 41 to the display 42 and causes the display 42 to display the MR image. Accordingly, a person who performs an MRI examination (doctor, engineer, or the like) can visually check the MR image displayed on the display 42 and diagnose whether or not the subject P has a lesion. The output control function 54 may transmit the MR image to, for example, a tablet terminal connected to the main body of the console device 40 via a network and cause a display device to display the MR image. The output control function 54 may display a GUI image or the like for receiving various operations by the operator of the MRI apparatus 1. Next, a configuration of the wireless RF coil 18 will be described. FIG. 2 is a diagram showing an example of the configuration and an example of connection of the wireless RF coil 18 according to the embodiment. FIG. 2 also shows an example of a more detailed configuration of the reception circuitry 35 that transmits/receives clock signals and sequence data to/from the wireless RF coil 18.

The transmission/reception circuitry 36 includes, for example, a data transmission circuitry 361, a clock transmission circuitry 362, and a data reception circuitry 363. The data transmission circuitry 361 transmits sequence data output by the sequence control circuitry 32 to the wireless RF coil 18. The clock transmission circuitry 362 transmits a clock signal generated by the clock generation circuitry 31 to the wireless RF coil 18. The data reception circuitry 363 receives MR data transmitted by the wireless RF coil 18. The data reception circuitry 363 outputs the received MR data to the sequence control circuitry 32. Each of the data transmission circuitry 361, the clock transmission circuitry 362, and the data reception circuitry 363 may individually include an antenna (not shown).

The wireless RF coil 18 includes, for example, a coil part 180, a data reception circuitry 181, a clock reception circuitry 182, a data transmission circuitry 183, a sequence execution circuitry 184, a phase synchronization circuitry 185, and an AD converter 186. The phase synchronization circuitry 185 includes, for example, a voltage controlled oscillator (VCO) 1851, a frequency divider 1852, a phase comparator 1853, and a loop filter 1854. The wireless RF coil 18 includes a battery (secondary battery) (not shown), such as a nickel-hydrogen battery, for example, as a power supply for each component. Further, the wireless RF coil 18 includes, for example, an antenna (not shown) for wireless communication with the transmission/reception circuitry 36.

The coil part 180 is a coil element attached to the subject P, or a coil array composed of a plurality of coil elements.

The coil part 180 outputs an MR signal (analog signal) emitted from the subject P according to the influence of a high frequency magnetic field generated by the RF coil 16 to the AD converter 186.

The data reception circuitry 181 receives sequence data transmitted by the data transmission circuitry 361. The data reception circuitry 181 outputs the received sequence data to the sequence execution circuitry 184. The data reception circuitry 181 may individually include an antenna (not shown), for example.

The clock reception circuitry 182 receives a clock signal transmitted by the clock transmission circuitry 362. The clock reception circuitry 182 outputs the received clock signal (hereinafter referred to as a "received clock signal RCLK") to the phase synchronization circuitry 185 (more specifically, the phase comparator 1853 included in the phase synchronization circuitry 185). The clock reception circuitry 182 may individually include an antenna (not shown), for example. The clock reception circuitry 182 is an example of a "clock receptor."

The data transmission circuitry 183 transmits the MR data output from the AD converter 186 to the transmission/reception circuitry 36 (more specifically, the data reception circuitry 363 included in the transmission/reception circuitry 36). The data transmission circuitry 183 may individually include an antenna (not shown), for example.

The sequence execution circuitry 184 executes an operation of imaging the subject P in synchronization with an event indicated by the sequence information executed by the sequence control circuitry 32 on the basis of the sequence data output by the data reception circuitry 181. More specifically, the sequence execution circuitry 184 operates the phase synchronization circuitry 185 and the AD converter 186 at each time on the basis of time information indicated in the sequence data. The sequence execution circuitry 184 may be, for example, a sequencer or processing circuitry having a processor such as a CPU. The sequence execution circuitry 184 is an example of a "second processing circuitry."

The phase synchronization circuitry 185 is a phase locked loop (PLL) that generates a clock signal CLK for operating components of the wireless RF coil 18. The phase synchronization circuitry 185 generates a clock signal CLK synchronized (phase-locked) with the received clock signal RCLK output from the clock reception circuitry 182. FIG. 2 shows a case where the clock signal CLK generated by the phase synchronization circuitry 185 is output to the AD converter 186. The phase synchronization circuitry 185 is an example of a "phase synchronizer."

The VCO 1851 is a voltage-controlled oscillator that generates a clock signal (hereinafter referred to as an "internal clock signal ICLK") having a frequency corresponding to a voltage. The VCO 1851 generates the internal clock signal ICLK having a frequency variable according to control of a voltage from the loop filter 1854. The VCO 1851 outputs the generated internal clock signal ICLK to the frequency divider 1852. The VCO 1851 is an example of a "clock generator."

The frequency divider 1852 divides the internal clock signal ICLK output from the VCO 1851 into the same frequency as the received clock signal RCLK. The frequency divider 1852 outputs the frequency-divided clock signal to the phase comparator 1853. The frequency divider 1852 is not limited to the configuration of dividing the internal clock signal ICLK, and may be configured to output a clock signal having the same frequency as the received clock signal RCLK to the phase comparator 1853 by multiplying the internal clock signal ICLK.

The phase comparator 1853 compares the phases of the received clock signal RCLK output by the clock reception circuitry 182 and the clock signal output by the frequency divider 1852 according to control of the sequence execution circuitry 184. The phase comparator 1853 outputs a signal representing the result of phase comparison (hereinafter referred to as a "phase comparison signal") to the loop filter 1854. The phase comparison signal is a signal that indicates whether the phase of the clock signal output from the frequency divider 1852 leads or lags the phase of the received clock signal RCLK. For example, the phase comparison signal is at a "High" level when the phase of the clock signal output from the frequency divider 1852 leads the phase of the received clock signal RCLK and is at a "Low" level when the phase of the clock signal lags the phase of the received clock signal RCLK.

The loop filter 1854 is a filter that can change the operating band during filtering. The loop filter 1854 is, for example, a low pass filter (LPF). The operating band of the loop filter 1854 can be changed to at least two bands, a wideband and a narrowband. The operating band of loop filter 1854 is switched by the sequence execution circuitry 184. The loop filter 1854 filters the phase comparison signal output from the phase comparator 1853 in the operating band switched according to control of the sequence execution circuitry 184 to convert the phase comparison signal into a substantially DC voltage signal. The loop filter 1854 outputs the voltage signal converted from the phase comparison signal to the VCO 1851. In other words, the loop filter 1854 feeds back the result of phase comparison in the phase comparator 1853 to the VCO 1851. Accordingly, the VCO 1851 generates the internal clock signal ICLK having a frequency corresponding to the voltage signal output from the loop filter 1854. The VCO 1851 outputs the generated internal clock signal ICLK to a component (AD converter 186 in FIG. 2) of the wireless RF coil 18 as the clock signal CLK phase-synchronized by the phase synchronization circuitry 185. The loop filter 1854 is an example of a "loop filter."

The AD converter 186 samples the analog MR signal output from the coil part 180 on the basis of the clock signal CLK output from the phase synchronization circuitry 185 to convert the analog MR signal into MR data, which is a digital MR signal. The AD converter 186 outputs the converted MR data to the data transmission circuitry 183. Accordingly, the data transmission circuitry 183 transmits the MR data to the data reception circuitry 363.

With such a configuration, the MRI apparatus 1 receives MR signals emitted from the subject P through the RF coil 16 and/or the wireless RF coil 18 and captures an MR image of the subject P. Here, in the MRI apparatus 1, the sequence control circuitry 32 can synchronize the wireless RF coil 18 with the gradient magnetic field power supply 33, the transmission circuitry 34, and the reception circuitry 35 by transmitting the clock signal generated by the clock generation circuitry 31 to the wireless RF coil 18 through the transmission/reception circuitry 36, thereby capturing a local MR image of the subject P. RF pulses (more specifically, a high frequency magnetic field generated by the RF coil 16 in response to the RF pulses) radiated to the subject P in order to capture an MR image in the MRI apparatus 1 is different from the frequency used in a wireless communication standard such as Wi-Fi through which the transmission/reception circuitry 36 performs transmission/reception to/from the wireless RF coil 18, for example, but is a high frequency. Therefore, it is conceivable that radiation of RF pulses may have some effect on wireless communication between the wireless RF coil 18 and the transmission/reception circuitry 36. In particular, it is conceivable that the clock signal transmitted even during the period in which the gradient magnetic field power supply 33, the transmission circuitry 34, and the reception circuitry 35 are driven in order to synchronize the operation of the wireless RF coil 18 is greatly affected by the RF pulses.

Therefore, the sequence execution circuitry 184 included in the wireless RF coil 18 controls generation of the clock signal CLK for operating each component included in 5 the wireless RF coil 18 on the basis of sequence data. That is, the sequence execution circuitry 184 controls the operation of the phase synchronization circuitry 185.

[Example of first control method for phase synchronization circuitry]

Figure 3:
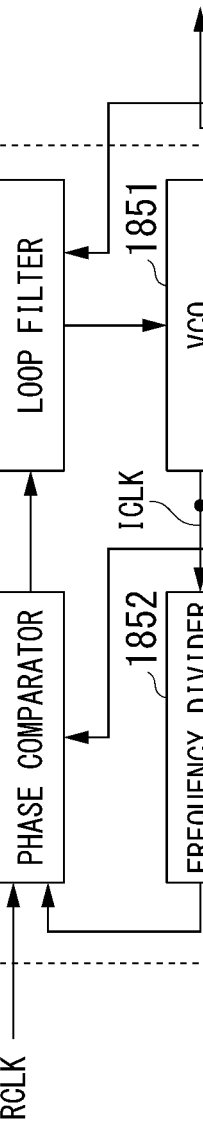
FIG. 3 is a diagram showing an example of a first control method for a phase synchronization circuitry in a sequence execution circuitry provided in the wireless RF coil according to the embodiment.
Figure 3:
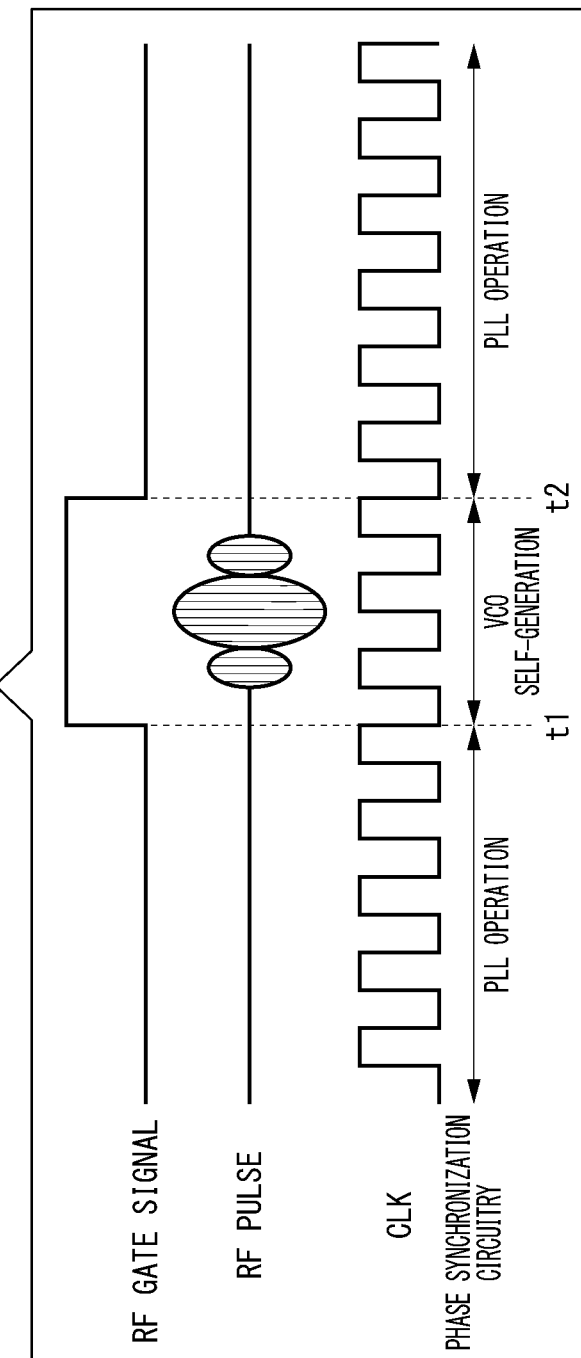

Here, an example of a method of controlling the phase synchronization circuitry 185 by the sequence execution circuitry 184 will be described. FIG. 3 is a diagram showing an example of a first control method for the phase synchronization circuitry 185 in the sequence execution circuitry 184 included in the wireless RF coil 18 according to an embodiment. FIG. 3 also shows the phase synchronization circuitry 185 related to generation of the clock signal CLK in the wireless RF coil 18 and a control timing by the sequence execution circuitry 184.

It is assumed that sequence data indicating a time t1 at which the RF coil 16 starts radiation of RF pulses and an RF pulse radiation period (a period from the time t1 to a time t2 at which radiation of the RF pulses ends) is input to the sequence execution circuitry 184. FIG. 3 shows the RF pulse radiation period as a period in which an RF gate signal is at a "high" level and schematically shows an example of a state in which RF pulses are actually radiated. The RF pulse radiation period is, for example, 200 [μs] to 1 [ms].

In this case, the sequence execution circuitry 184 causes the phase comparator 1853 to perform phase comparison during a period before the time t1. Accordingly, the received clock signal RCLK, that is, the internal clock signal ICLK for a phase locked loop operation (hereinafter referred to as a "PLL operation") synchronized in phase with the clock signal generated by the clock generation circuitry 31 is output from the phase synchronization circuitry 185 as the clock signal CLK. Then, the sequence execution circuitry 184 stops phase comparison of the phase comparator 1853 at the time t1. Accordingly, the loop filter 1854 outputs a fixed voltage signal to the VCO 1851, and the internal clock signal ICLK generated (self-generated) by the VCO 1851 itself is output as it is as the clock signal CLK from the phase synchronization circuitry 185. Thereafter, the sequence execution circuitry 184 causes the phase comparator 1853 to perform phase comparison again at the time t2. That is, the sequence execution circuitry 184 restores the PLL operation of the phase synchronization circuitry 185 from the stopped state. Accordingly, the internal clock signal ICLK for the PLL operation synchronized in phase with the received clock signal RCLK is output again from the phase synchronization circuitry 185 as the clock signal CLK.

In this manner, the sequence execution circuitry 184 stops the phase comparison operation in the phase comparator 1853 during the RF pulse radiation period (during the period in which the RF gate signal is at a "high" level). Accordingly, the phase synchronization circuitry 185 can output the clock signal CLK that is not affected by radiation of RF pulses in the RF coil 16 without phase synchronization with the received clock signal RCLK whose cycle is likely to be disturbed (jitter is likely to increase) due to some influence on wireless communication between the wireless RF coil 18 and the transmission/reception circuitry 36 during the period in which the RF coil 16 radiates RF pulses.

Although FIG. 3 shows a control method when RF pulses are radiated once, radiation of RF pulses is performed a plurality of times in imaging of the subject P in the MRI apparatus 1. Therefore, the sequence execution circuitry 184 repeats the first control method shown in FIG. 3 for each RF pulse radiation period (RF gate signal) to control the operation of the phase synchronization circuitry 185.

It is also conceivable that the phase of the clock signal CLK (the internal clock signal ICLK self-generated by the VCO 1851) output by the phase synchronization circuitry 185 gradually deviates from the clock signal generated by the clock generation circuitry 31 during the period in which the phase comparator 1853 stops phase synchronization, that is, during the period in which the phase synchronization circuitry 185 does not perform the PLL operation. However, the sequence execution circuitry 184 causes the phase comparator 1853 to perform phase comparison again at the time t2 at which the period during which the RF coil 16 radiates RF pulses ends. Therefore, even if the phase of the clock signal CLK gradually deviates from the phase of the clock signal generated by the clock generation circuitry 31, the result of phase comparison is fed back to the VCO 1851 from the time when the sequence execution circuitry 184 causes phase comparison to be executed, and thus phase deviation is eliminated in a short period of time and the phase synchronization circuitry 185 outputs the phase-synchronized (phase-locked) clock signal CLK again.

[Example of second control method for phase synchronization circuitry]

Figure 4:
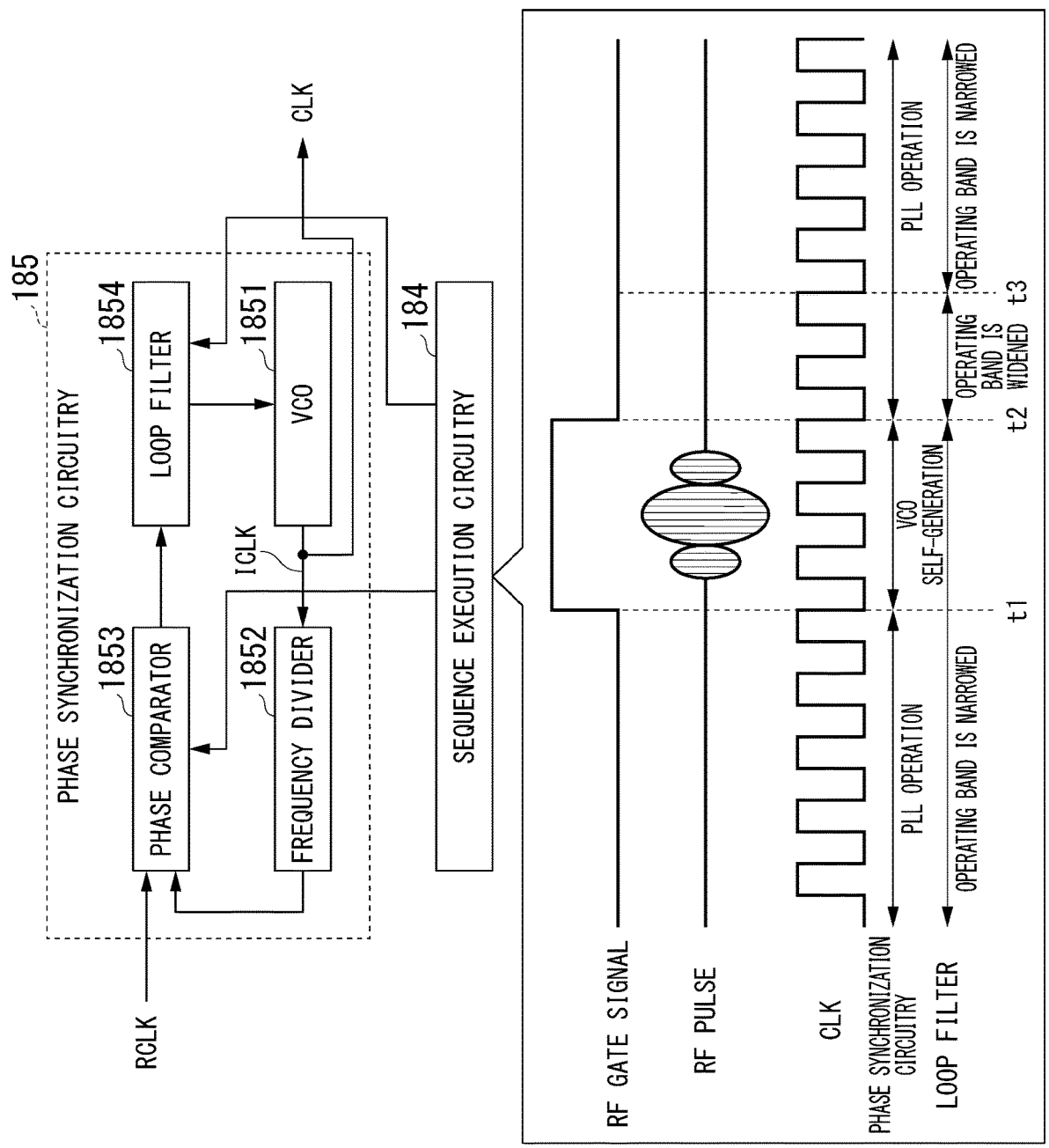
FIG. 4 is a diagram showing an example of a second control method for the phase synchronization circuitry in the sequence execution circuitry provided in the wireless RF coil according to the embodiment.

Here, an example of a control method in a case where the sequence execution circuitry 184 controls the phase synchronization circuitry 185 on the assumption that the sequence execution circuitry 184 causes the phase comparator 1853 to perform phase comparison again, but phase deviation is not eliminated in a short period of time, for example, will be described. FIG. 4 is a diagram showing an example of a second control method for the phase synchronization circuitry in the sequence execution circuitry 184 included in the wireless RF coil 18 according to an embodiment. FIG. 4 also shows the phase synchronization circuitry 185 related to generation of the clock signal CLK in the wireless RF coil 18 and a control timing by the sequence execution circuitry 184. In the second control method shown in FIG. 4, the sequence execution circuitry 184 also switches the operating band of the loop filter 1854 in addition to the first control method shown in FIG. 3. That is, in the second control method shown in FIG. 4, a method by which the sequence execution circuitry 184 controls the phase comparator 1853 is the same as the first control method shown in FIG. 3. Therefore, re-description of the method by which the sequence execution circuitry 184 controls the phase comparator 1853 will be omitted.

In this case, the sequence execution circuitry 184 narrows the operating band of the loop filter 1854 during a period before the time t2. Accordingly, the phase synchronization circuitry 185 outputs the internal clock signal ICLK for the PLL operation, which has the phase synchronized with the phase of the received clock signal RCLK with higher accuracy as the clock signal CLK. Then, the sequence execution circuitry 184 widens the operating band of the loop filter 1854 at the time t2. Accordingly, in the phase synchronization circuitry 185, even if the phase of the clock signal CLK has gradually deviated due to stopping of phase comparison of the phase comparator 1853 between the time t1 and the time t2, the state of the PLL operation can approach a state equivalent to the phase-locked state more rapidly by widening the operating band of the loop filter 1854 although the accuracy is lower than when the operating band is narrowed. That is, by widening the operating band of the loop filter 1854, the time required to fall within a predetermined phase difference in the phase synchronization circuitry 185 can be reduced. Thereafter, the sequence execution circuitry 184 narrows the operating band of the loop filter 1854 again at a time t3. Accordingly, the internal clock signal ICLK for the PLL operation synchronized with the phase of the received clock signal RCLK with higher accuracy is output again from the phase synchronization circuitry 185 as the clock signal CLK. The period from the time t2 to the time t3 in which the operating band of the loop filter 1854 is widened may be, for example, a predetermined period such as a time required for the phase synchronization circuitry 185 to start the phase synchronization operation (PLL operation) until phase synchronization converges (phase is locked). As to the period from the time t2 to the time t3 in which the operating band of the loop filter 1854 is widened, for example, the amount of phase deviation between the received clock signal RCLK and the internal clock signal ICLK is detected, and a time when the amount of phase deviation has become a predetermined amount of deviation or less is set to the time t3. The amount of phase deviation between the received clock signal RCLK and the internal clock signal ICLK may be detected, for example, by determining a phase comparison signal output by the phase comparator 1853, or on the basis of a voltage signal output from the loop filter 1854.

In this manner, the sequence execution circuitry 184 widens the operating band of the loop filter 1854 for a predetermined period (period between the time t2 and the time t3) at the time of restoring the PLL operation of the phase synchronization circuitry 185 when it is assumed that phase deviation between the received clock signal RCLK and the internal clock signal ICLK will not be eliminated in a short period of time. Accordingly, in the phase synchronization circuitry 185, it is possible to approach a state in which a phase is synchronized within a predetermined phase difference more rapidly as compared to a case where the operating band of the loop filter 1854 is not changed (a case where it remains narrow).

Although FIG. 4 also shows a control method when RF pulses are radiated once, the sequence execution circuitry 184 repeats the second control method shown in FIG. 4 for each RF pulse radiation period (RF gate signal) in which RF pulses are radiated a plurality of times when the subject P is imaged in the MRI apparatus 1 to control the operation of the phase synchronization circuitry 185.

Considering that the phase of the internal clock signal ICLK gradually deviates from the phase of the clock signal generated by the clock generation circuitry 31, as described above, it is conceivable that the period in which the phase synchronization circuitry 185 does not perform the PLL operation (the period in which the phase comparator 1853 stops phase synchronization) should be as short as possible.

Therefore, the sequence execution circuitry 184 may adjust the timing and the period for causing the phase synchronization circuitry 185 to stop the PLL operation.
[Example of third control method for phase synchronization circuitry]

Figure 5:
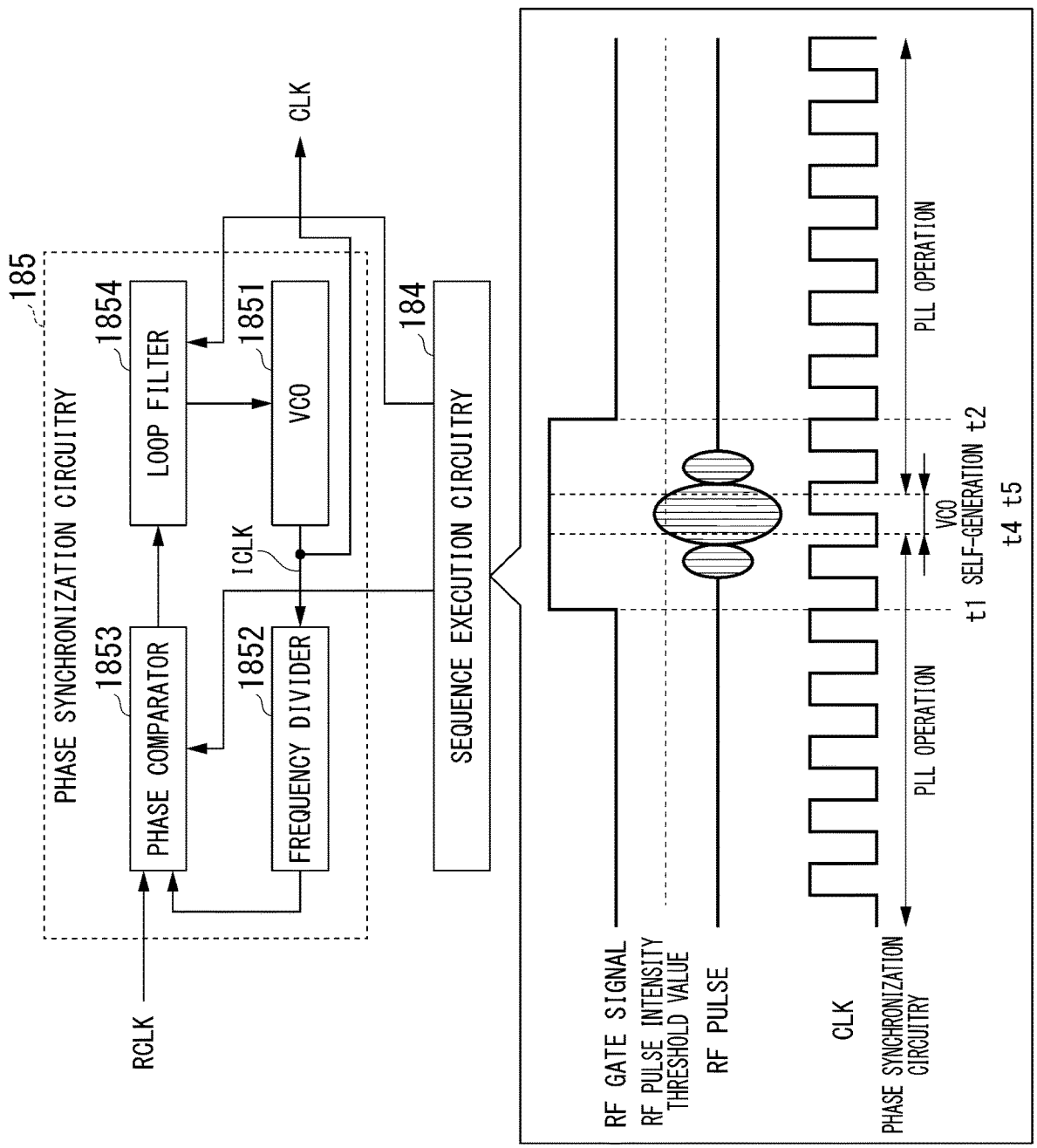
FIG. 5 is a diagram showing an example of a third control method for the phase synchronization circuitry in the sequence execution circuitry provided in the wireless RF coil according to the embodiment.

Here, an example of a control method in a case where the period during which the phase comparator 1853 stops phase synchronization is reduced will be described. FIG. 5 is a diagram showing an example of a third control method for the phase synchronization circuitry 185 in the sequence execution circuitry 184 included in the wireless RF coil 18 according to an embodiment. FIG. 5 also shows the phase synchronization circuitry 185 related to generation of the clock signal CLK in the wireless RF coil 18 and a control timing by the sequence execution circuitry 184. In the third control method shown in FIG. 5, the control method of the sequence execution circuitry 184 for causing the phase synchronization circuitry 185 to perform the PLL operation or to stop the PLL operation is also the same as the first control method shown in FIG. 3. Therefore, re-description of the method by which the sequence execution circuitry 184 controls the phase synchronization circuitry 185 will be omitted.

For example, it is assumed that sequence data indicating a time t4 until which RF pulses to be radiated within the radiation period become equal to or greater than an intensity (RF pulse intensity threshold value) that can be considered to have some influence on wireless communication between the wireless RF coil 18 and the transmission/reception circuitry 36, and a time t5 representing a period during which RF pulses having the RF pulse intensity threshold value or more are radiated are input to the sequence execution circuitry 184 in addition to the time t1 at which the RF coil 16 starts radiation of RF pulses and the time t2 representing the RF pulse radiation period. Although the RF pulse intensity threshold value is the intensity of RF pulses determined depending on whether or not it affects wireless communication, the timings of the time t4 and the time t5 are determined by a result of preliminary imaging that is performed as a stage before starting imaging (diagnosis) of the subject P and determines the intensity of RF pulses to be radiated, the physique of the subject P, and the like. Therefore, the timings of the time t4 and the time t5 may not be determined if an MR image necessary for diagnosis can be captured without radiating RF pulses having an intensity equal to or greater than the RF pulse intensity threshold value at the time of diagnosing the subject P. The time t4 is an example of a "first elapsed time" and the time t5 is an example of a "second elapsed time."

The sequence execution circuitry 184 causes the phase synchronization circuitry 185 to perform a PLL operation in a period before the time t4 to output the internal clock signal ICLK phase-synchronized with the received clock signal RCLK as the clock signal CLK. Then, the sequence execution circuitry 184 causes the phase synchronization circuitry 185 to stop the PLL operation and output the internal clock signal ICLK self-generated by the VCO 1851 as the clock signal CLK at the time t4. Thereafter, the sequence execution circuitry 184 restores the phase synchronization circuitry 185 from the state in which the PLL operation was stopped at the time t5.

In this manner, the sequence execution circuitry 184 causes the phase synchronization circuitry 185 to stop the PLL operation only during a period in which RF pulses having the RF pulse intensity threshold value or more which can be considered to have some influence on wireless communication between the wireless RF coil 18 and the transmission/reception circuitry 36 are radiated in the RF pulse radiation period (period in which the RF gate signal is at a "high" level). Accordingly, it is possible to reduce the period in which the internal clock signal ICLK self-generated by the VCO 1851 is output from the phase synchronization circuitry 185 as the clock signal CLK.

Although FIG. 5 also shows a control method when RF pulses are radiated once, the sequence execution circuitry 184 repeats the third control method shown in FIG. 5 for each RF pulse radiation period (RF gate signal) in which RF pulses are radiated a plurality of times when the subject P is imaged in the MRI apparatus 1 to control the operation of the phase synchronization circuitry 185.

In the third control method shown in FIG. 5, a case in which the sequence execution circuitry 184 stops the PLL operation of the phase synchronization circuitry 185 on the basis of the intensity of RF pulses equal to or higher than the RF pulse intensity threshold value, that is, the peak height of RF pulses is represented. However, adjustment of the period during which the sequence execution circuitry 184 outputs the self-generated internal clock signal ICLK as the clock signal CLK is not limited to the intensity of RF pulses. For example, the sequence execution circuitry 184 may perform control to stop the PLL operation of the phase synchronization circuitry 185 when an RF pulse radiation time is equal to or greater than a predetermined length, that is, on the basis of the width of the RF pulse to be radiated.

In the third control method shown in FIG. 5, an example of a case in which the sequence execution circuitry 184 stops or restores the PLL operation in the phase synchronization circuitry 185 on the basis of the time t4 and the time t5 at which RF pulses become equal to or greater than the RF pulse intensity threshold value indicated in the sequence data transmitted by the control device 30 through wireless communication is represented. However, the wireless RF coil 18 can also be configured to detect whether or not RF pulses are equal to or greater than the RF pulse intensity threshold value.

Figure 6:
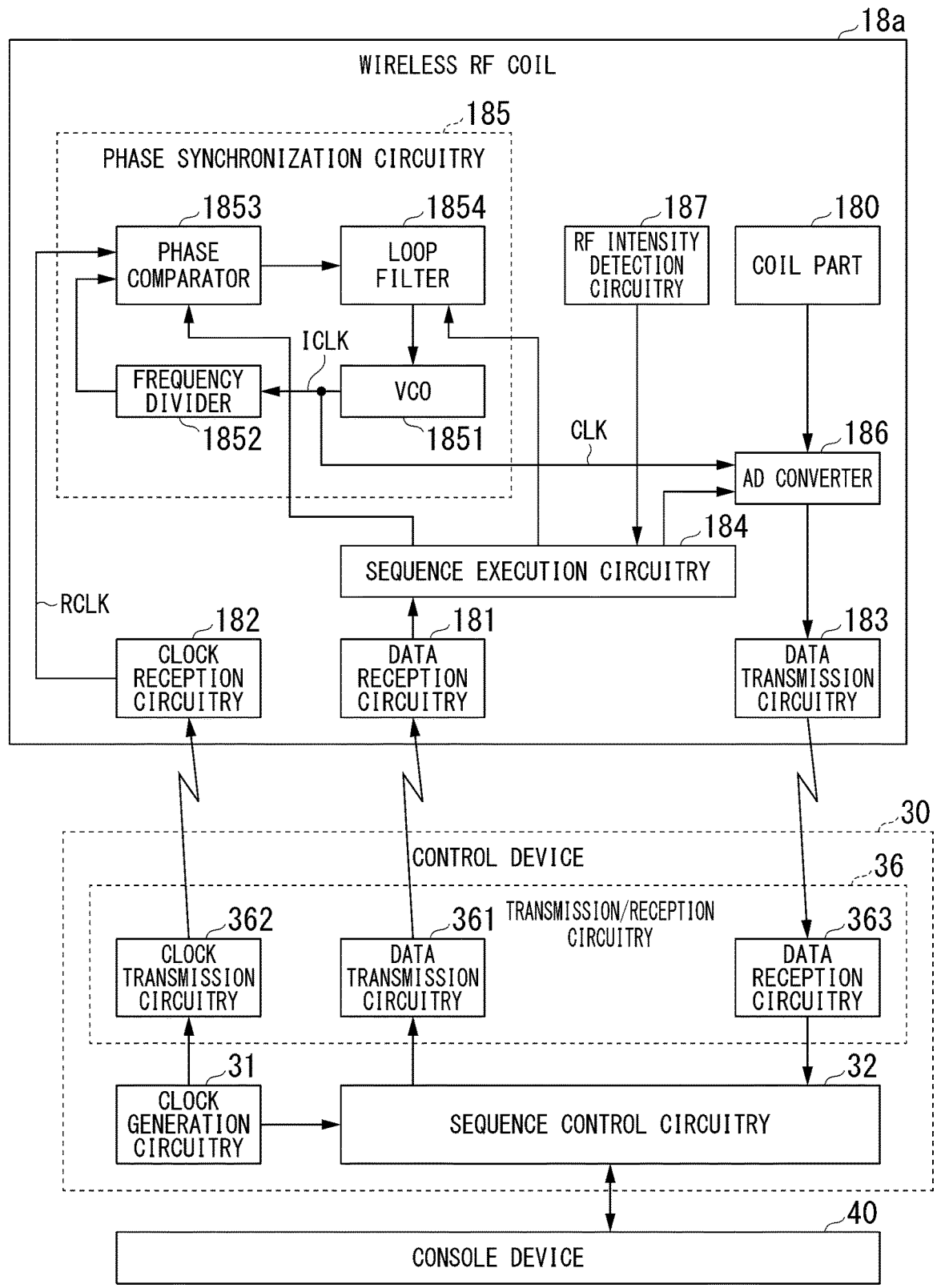
FIG. 6 is a diagram showing an example of another configuration and an example of connection of the wireless RF coil according to the embodiment.

Here, an example of the wireless RF coil 18 configured to detect the intensity of RF pulses will be described. FIG. 6 is a diagram showing an example of another configuration and an example of connection of the wireless RF coil 18 according to the embodiment. Although FIG. 6 also shows an example of a more detailed configuration of the reception circuitry 35 that transmits/receives a clock signal and sequence data to/from the wireless RF coil 18 having another configuration (hereinafter referred to as a "wireless RF coil 18a"), the configuration of the reception circuitry 35 is the same as the configuration for transmission/reception to/from the wireless RF coil 18 and thus detailed description thereof will be omitted.

The wireless RF coil 18a includes, for example, the coil part 180, the data reception circuitry 181, the clock reception circuitry 182, the data transmission circuitry 183, the sequence execution circuitry 184, the phase synchronization circuitry 185, the AD converter 186, and an RF intensity detection circuitry 187. The wireless RF coil 18a has a configuration in which the RF intensity detection circuitry 187 is added to the wireless RF coil 18. In the wireless RF coil 18a, the same components as those of the wireless RF coil 18 are denoted by the same reference numerals. Therefore, in the components included in the wireless RF coil 18a, detailed description of components having the same configurations and operations as those of the components included in the wireless RF coil 18 will be omitted, and only different configurations and operations will be described.

The RF intensity detection circuitry 187 detects the intensity of RF pulses (more specifically, a high frequency magnetic field generated by the RF coil 16 in response to the RF pulses) radiated to the subject P in order to capture an MR image in the MRI apparatus 1. For example, the RF intensity detection circuitry 187 has an RF pulse intensity threshold value set therein in advance, and when detecting RF pulses having an intensity equal to or higher than the RF pulse intensity threshold value, outputs a detection signal indicating this fact to the sequence execution circuitry 184.

Accordingly, the sequence execution circuitry 184 performs the same control on the phase synchronization circuitry 185 as that performed at the time t4 and the time t5 shown in FIG. 5 on the basis of the detection signal output from the RF intensity detection circuitry 187. That is, the sequence execution circuitry 184 causes the phase synchronization circuitry 185 to stop the PLL operation while the RF intensity detection circuitry 187 outputs the detection signal indicating that RF pulses having an intensity equal to or greater than the RF pulse intensity threshold value have been detected. The RF intensity detection circuitry 187 is an example of an "RF intensity detector."

Accordingly, on the basis of the intensity of RF pulses detected by the wireless RF coil 18a itself, the wireless RF coil 18a can set the period during which the internal clock signal ICLK self-generated by the VCO 1851 is output from the phase synchronization circuitry 185 as the clock signal CLK to a suitable period that matches a period during which RF pulses actually greatly affect.

As described above, in the MRI apparatus 1 which is a magnetic resonance imaging apparatus of the embodiment, a clock signal and sequence data are transmitted to the wireless RF coil 18 which is a wireless local coil through wireless communication, and MR data transmitted by the wireless RF coil 18 through wireless communication is received. Then, in the MRI apparatus 1 of the embodiment, the wireless RF coil 18 performs an operation of imaging the subject P in synchronization with imaging performed in the main body of the MRI apparatus 1 on the basis of the sequence data transmitted through wireless communication. Here, in the MRI apparatus 1 of the embodiment, if RF pulses radiated by the RF coil 16 in order to image the subject P are likely to affect the clock signal transmitted to the wireless RF coil 18 through wireless communication, the operation (PLL operation) of phase synchronization between the received clock signal RCLK and the internal clock signal ICLK self-generated in the wireless RF coil 18 is stopped during that period. As a result, the clock signal CLK for operating the wireless RF coil 18 becomes a stable clock signal that is not affected by RF pulse radiation in the RF coil 16. Accordingly, it is possible to capture a more suitable MR image by the wireless RF coil 18 of wireless type in the MRI apparatus 1 of the embodiment.

According to at least one embodiment described above, the transmission coil (16) that radiates RF pulses to the subject (P), the reception coil (18) that receives magnetic resonance signals from the subject, and a first processing circuitry (30) that controls the transmission coil and the reception coil are provided, the reception coil includes the clock receptor (182) that receives a clock signal wirelessly transmitted by the first processing circuitry, the phase synchronizer (185) that performs phase synchronization with the clock signal, and a second processing circuitry (184) that controls the phase synchronizer, and the second processing circuitry can reduce the influence of the RF pulses on the clock signal in the wireless type RF coil (18) by switching operating states of the phase synchronizer in accordance with a radiation timing of the RF pulses when the RF coil (16) of the magnetic resonance imaging apparatus is made wireless.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions. Regarding the above embodiments, the following supplements are disclosed as one aspect and optional features of the invention.

(Supplement 1)

A magnetic resonance imaging apparatus including:

a transmission coil that radiates RF pulses to a subject;

a reception coil that receives magnetic resonance signals from the subject; and first processing circuitry that controls the transmission coil and the reception coil, wherein the reception coil includes:

a clock receptor that receives a clock signal wirelessly transmitted by the first processing circuitry;

a phase synchronizer that performs phase synchronization with the clock signal; and second processing circuitry that controls the phase synchronizer, and wherein the second processing circuitry switches operating states of the phase synchronizer in accordance with a radiation timing of the RF pulses.

(Supplement 2)

The phase synchronizer may include a clock generator that generates an internal clock signal, and the second processing circuitry may stop the phase synchronization in the phase synchronizer in accordance with the radiation timing of the RF pulses and output the internal clock signal generated by the clock generator from the phase synchronizer.

(Supplement 3)

The phase synchronizer may include a loop filter having a changeable operating band, and the second processing circuitry may widen the operating band of the loop filter at the time of restoring the phase synchronization in the phase synchronizer from a stopped state.

(Supplement 4)

The second processing circuitry may narrow the operating band of the loop filter when a time required for convergence of the phase synchronization in the phase synchronizer has elapsed after widening the operating band of the loop filter.

(Supplement 5)

The second processing circuitry may adjust a period for stopping the phase synchronization in the phase synchronizer based on the intensity of the radiated RF pulses.

(Supplement 6)

The second processing circuitry may stop the phase synchronization in the phase synchronizer based on a first elapsed time from the start of radiation of the RF pulses and restore the phase synchronization from the stopped state based on a second elapsed time after the first elapsed time.

(Supplement 7)

The reception coil includes an RF intensity detector that detects the intensity of the radiated RF pulses, and the second processing circuitry may stop the phase synchronization in the phase synchronizer when the RF intensity detector detects the intensity of the RF pulses which is equal to or greater than a threshold value and restore the phase synchronization from the stopped state when the RF intensity detector detects the intensity of the RF pulses which is less than the threshold value.

(Supplement 8)

The second processing circuitry may control the operating states of the phase synchronizer based on time information indicating radiation timings of the RF pulses in chronological order based on a time at which imaging of the subject is started, which is wirelessly transmitted by the first processing circuitry before imaging of the subject is started.

What is claimed is:

1. A magnetic resonance imaging apparatus comprising:

a transmission coil configured to radiate RF pulses to a subject;

a reception coil configured to receive magnetic resonance signals from the subject; and first processing circuitry configured to control the transmission coil and the reception coil, wherein the reception coil includes:

a clock receptor configured to receive a clock signal wirelessly transmitted by the first processing circuitry;

a phase synchronizer configured to perform phase synchronization with the clock signal; and second processing circuitry configured to control the phase synchronizer, and wherein the second processing circuitry switches operating states of the phase synchronizer in accordance with a radiation timing of the RF pulses.

2. The magnetic resonance imaging apparatus according to claim 1, wherein the phase synchronizer includes a clock generator configured to generate an internal clock signal, and the second processing circuitry stops the phase synchronization in the phase synchronizer in accordance with the radiation timing of the RF pulses and outputs the internal clock signal generated by the clock generator from the phase synchronizer.

3. The magnetic resonance imaging apparatus according to claim 2, wherein the phase synchronizer includes a loop filter configured to changeable operating band, and the second processing circuitry widens the operating band of the loop filter at the time of restoring the phase synchronization in the phase synchronizer from a stopped state.

4. The magnetic resonance imaging apparatus according to claim 3, wherein the second processing circuitry narrows the operating band of the loop filter when a time required for convergence of the phase synchronization in the phase synchronizer has elapsed after widening the operating band of the loop filter.

5. The magnetic resonance imaging apparatus according to claim 2, wherein the second processing circuitry adjusts a period for stopping the phase synchronization in the phase synchronizer based on an intensity of the radiated RF pulses.

6. The magnetic resonance imaging apparatus according to claim 5, wherein the second processing circuitry stops the phase synchronization in the phase synchronizer based on a first elapsed time from the start of radiation of the RF pulses and restores the phase synchronization from the stopped state based on a second elapsed time after the first elapsed time.

7. The magnetic resonance imaging apparatus according to claim 5, wherein the reception coil includes an RF intensity detector configured to detect the intensity of the radiated RF pulses, and the second processing circuitry stops the phase synchronization in the phase synchronizer when the RF intensity detector detects the intensity of the RF pulses which is equal to or greater than a threshold value and restores the phase synchronization from the stopped state when the RF intensity detector detects the intensity of the RF pulses which is less than the threshold value.

* * * * *